United States Patent [19]

Lane et al.

[11] Patent Number: 5,419,900

[45] Date of Patent: May 30, 1995

[54] IMMUNOLOGIC ENHANCEMENT WITH INTERMITTENT INTERLEUKIN-2 THERAPY

[75] Inventors: H. Clifford Lane, Bethesda; Joseph A. Kovacs, Potomac, both of Md.

[73] Assignee: The United States of America as represented by the Department of of Health and Human Services, Washington, D.C.

[21] Appl. No.: 63,315

[22] Filed: May 19, 1993

[51] Int. Cl.$^6$ .................. A61K 38/20; A01N 43/48
[52] U.S. Cl. .................. 424/85.2; 514/50; 514/885
[58] Field of Search .................. 514/49, 885, 50; 424/85.2

[56] References Cited

U.S. PATENT DOCUMENTS

| | | | |
|---|---|---|---|
| 4,866,157 | 9/1989 | Durette | 514/19 |
| 4,908,433 | 3/1990 | Mertelsmann et al. | 530/351 |
| 5,026,687 | 6/1991 | Yarchoan et al. | 514/45 |

FOREIGN PATENT DOCUMENTS

| | | |
|---|---|---|
| 343480 | 11/1983 | European Pat. Off. . |
| 426521 | 5/1991 | European Pat. Off. . |
| 452598 | 10/1991 | European Pat. Off. . |

OTHER PUBLICATIONS

Stein et al, J. Infect. Dis 165: 352–363, 1993.
Schwartz et al, J. Acquir Immune Defic Syndr 4(1): 11–23, 1991 (abstract only provided).
Schwartz et al, Biotherapy 2: 119–136, 1990.
Oyazu et al, PNAS 87: 2379–2383, 1990.
Matory et al, Journal of Biological Response Modifiers 4: 377–390, 1985.
Fauser A. A., J. of Cellular Biochemistry 45: 353–358, 1991.
Genzyme Catalog, Cytokine Research Products 1991 pp. 19 & 20.
H. Teppler, et al., *J. Infect. Dis.* 167: 291–298 (1993).
H. Teppler, et al., *J. Exp. Med.* 177: 483–492 (1993).
S. A. Rosenberg et al, *J. Natl Cancer Inst.* 85(8): 622–632 (1993).
Lane, et al., *J. Biol. Response Mos.* 3: 512–516 (1984).
West, "Lymphokine-Activated Killer Lymphocytes: Biotherapeutice Clinical Trials," *Imm. Ser.* 48: 79–92 (1989).
Schwartz et al., "Safety and Effects of Interleukin-2 Plus Zidovudine in Asymptomatic Individuals Infected with Human Immunodeficiency Virus," *J. Acq. Imm. Def. Synd.* 4(1): 11–23 (1991).

*Primary Examiner*—Christine M. Nucker
*Assistant Examiner*—Julie Krsek-Staples
*Attorney, Agent, or Firm*—Foley & Lardner

[57] ABSTRACT

A method for activating a mammalian immune system entails a series of continuous IL-2 infusions that are effected intermittently over an extended period. For example, IL-2 can be administered continuously for a period that is on the order of 5 days in length, and successive infusions of this nature can be separated by a period of at least 4 weeks. Sustained beneficial effects, including elevated CD4 cell counts, restoration of lymphocyte function and an increase in the number of IL-2 receptors, are achieved with such intermittent IL-2 therapy, which can be combined with another therapy which targets a specific disease state, such as an antiretroviral therapy comprising, for example, the administration of AZT, ddI or interferon alpha.

5 Claims, 9 Drawing Sheets

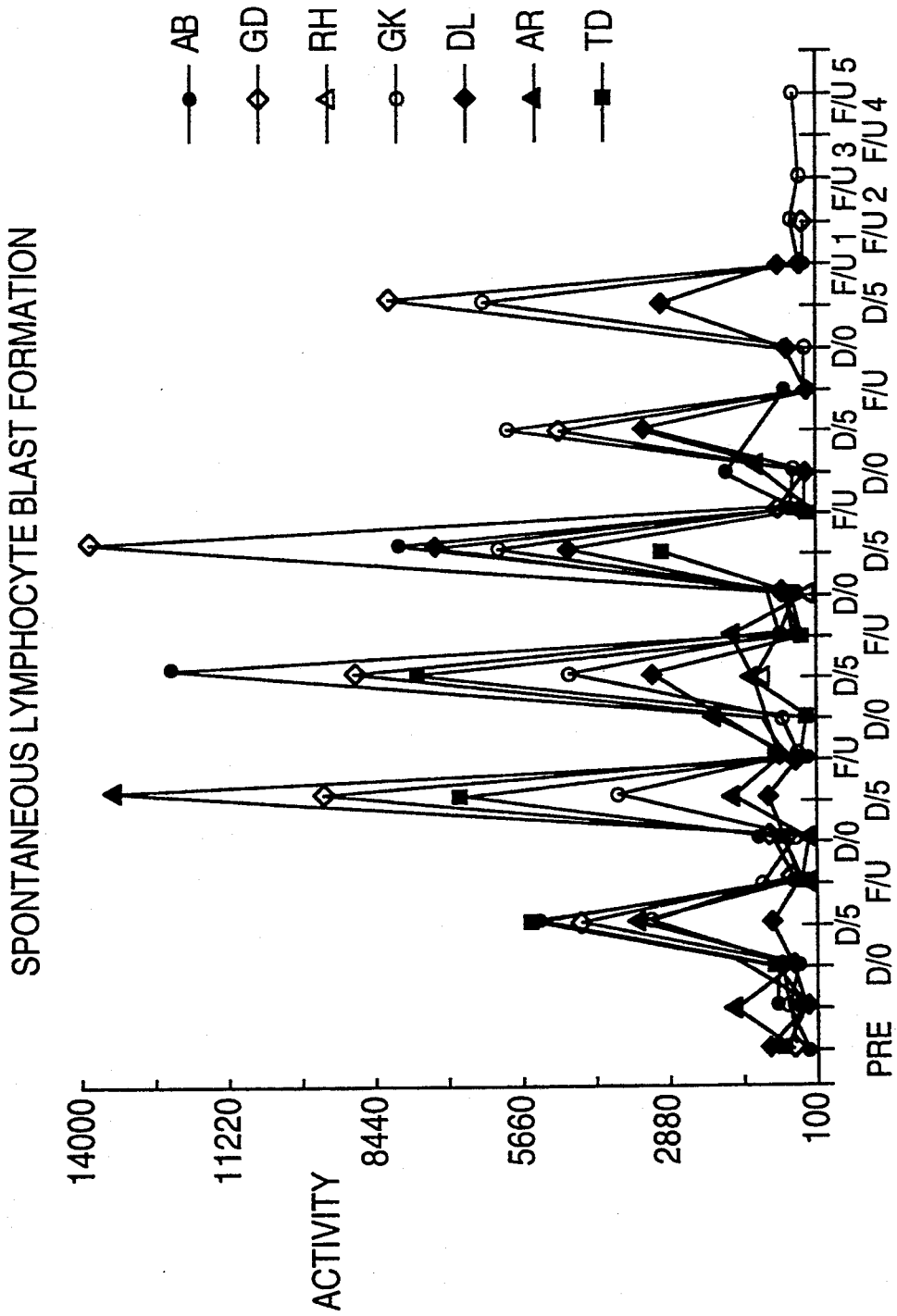

IMMUNOLOGIC ENHANCEMENT WITH INTERMITTENT INTERLEUKIN-2 THERAPY

Work relating to this invention was supported in part with federal funds under contract number N01-AI-05058 from the National Institute of Allergy and Infectious Disease (NIAID), National Institutes of Health.

BACKGROUND OF THE INVENTION

The present invention pertains to a method for activating the immune system of a patient by intermittently administering interleukin-2 (IL-2) to that patient. Such administration of IL-2 can optionally be combined with other therapies, e.g., anti-retroviral, anti-bacterial, or anti-fungal therapies, suitable for treatment of the patient's condition. This invention also relates to an approach to gene therapy that entails the use of IL-2 given to a patient so as to facilitate in situ lymphocyte transduction by a retroviral vector also administered to the same patient.

Attempts at immune activation and restoration in the past have utilized bone marrow transplantation or lymphocyte transfers (H. C. Lane et al., Ann. Internal Med. 113: 512–519 (1990)), immunomodulating agents such as immuthiol (J. M. Lang et al., Lancet 24: 702–706 (1988)) or isoprinosine (C. Pedersen et al., N. Engl. J. Med. 322: 1757–1763 (1990)), and recombinant cytokines such as interferon alpha (IFN-$\alpha$) (H. C. Lane et al., Ann. Intern. Med. 112: 805–811 (1990)) or IL-2. H. C. Lane et al., J. Biol. Response Mod. 3, 512–516 (1984); D. H. Schwartz et al., J. Acquir. Immune Defic. Syndr. 4, 11–23 (1991); P. Mazza et al., Eur. J. Haematol. 49: 1–6 (1992); H. W. Murray et al., Am. J. Med. 93: 234 (1992); H. Teppler et al., J. Infect. Dis. 167: 291–298 (1993); P. Volherding et al., AIDS Res. Hum. Retroviruses 3: 115–124 (1987). These studies have resulted in minimal or transient immune system restoration.

The use of biologic response modifiers in general, and of IL-2 in particular, is an active area of clinical research. Interleukin-2 is a T cell-derived lymphokine with a number of immunomodulating effects including activation, as well as induction of proliferation and differentiation, of both T and B lymphocytes (K. A. Smith, Science 140: 1169–1176 (1988)). Exogenous IL-2 has been shown in vitro to increase the depressed natural killer cell activity and cytomegalovirus-specific cytotoxicity of peripheral blood mononuclear cells from patients with AIDS (A. H. Rook et al., J. Clin. Invest. 72: 398–403 (1983)), as well as to increase IFN-$\gamma$ production by lymphocytes from patients with AIDS (H. W. Murray et al., Ioc. cit. 76: 1959–1964 (1985)).

IL-2 given by high dose infusion has been employed in the treatment of renal cell carcinoma and melanoma (J. Natl. Cancer Inst. 85(8): 622–632 (1993)). For example, doses of 36 million international units (MU) given continuously over a period of 24 hours has been used in the treatment of cancer (18MU is equivalent to about 1 mg protein). Lancet 340: 241 (1992). The use of high doses of IL-2 generally is not well tolerated by patients, however, and side effects are more pronounced at such high levels.

Other researchers are evaluating IL-2 in the treatment of other diseases, including HIV infection. The use of lower doses of IL-2 in a continuous therapy regime has been disclosed by Yarchoan et al., U.S. Pat. No. 5,026,687. More specifically, Yarchoan et al. teach the use of the anti-retroviral agent ddI in combination with IL-2 administered continuously at a dosage between 25,000 to 1 million international units (U) per day, for a period of three months. While Yarchoan et al. predict that "beneficial results" will accompany the combined ddI/IL-2 regimen, they do not attribute these results to IL-2 per se. Moreover, although dosages at this lower level have been shown to cause initial increases in CD4 levels, these increases were transient in nature, i.e., CD4 levels returned to baseline within 6 months after the completion of the treatment.

Many researchers feel that the use of IL-2 is contraindicated in patients with HIV infection due to its potential to activate HIV. No method of treatment of HIV with IL-2 has been disclosed which results in a sustained response, or which yields long-term beneficial results.

Cells that have been stimulated to actively synthesize DNA are susceptible to transduction by gene transfer therapy. Present methods of gene therapy require a complicated, in vitro transformation. More specifically, cells are removed from a patient, activated in vitro, and used to establish cell lines which are then gene-transduced in vitro and reimplanted in the patient. This procedure is expensive, and its success its limited due to the potential of failure at each of the steps of activating the cells, effecting the transduction, and implanting the cells in the patient for expression.

Attempts at using retroviral vectors to effect in vivo gene transfer have been limited. Retroviruses will only integrate stably into target cells that are actively synthesizing DNA. This integration must occur before retroviral gene expression can be effected. Because only a fraction of cells are actively producing DNA at any giving time, such in vivo gene transfer methods have shown little success.

SUMMARY OF THE INVENTION

It is therefore an object of the present invention to provide a means for activating the immune system that employs IL-2 but that avoids the pronounced side-effects associated with conventional IL-2 treatments.

It is also an object of the present invention to provide a methodology suitable for treating a wide variety of disease states, including HIV infection, through the use of IL-2 therapy.

It is a further object of the present invention to provide an approach to effecting retroviral vector-mediated transduction in situ, in the context of gene therapy, for a patient whose immune system has been activated by the administration of IL-2.

In accomplishing these and other objects, there has been provided, in accordance with one aspect of the present invention, a method for activating the immune system of a patient, comprising the step of administering an amount of IL-2 to the patient that is sufficient to increase the level of helper/inducer T-cell function in the patient, as gauged, for example, by an increased CD4 count or an increase in expression of IL-2 receptors in the patient.

In a preferred embodiment, the IL-2 is administered in a series of infusions effected intermittently, with each of said infusions being continuous over a period of time of from 1 day to 2 weeks, and with successive infusions being separated by a period of time of at least 4 weeks. In another preferred embodiment, administration of IL-2 is combined with a therapy administered to the patient, prior to or concomitantly with administering of IL-2, which targets a specific disease state, such as a disease state that comprises an infection of the patient by a pathogen against which a cellular immune response is the principal mechanism for specific immunity therefor in the patient. The disease state may comprise a secondary infection of the patient, where the patient has a suppressed immune system.

In accordance with another aspect of the present invention, a process has been provided for modulating the immune system of a patient. This process comprises the steps of activating the immune system by the use of IL-2 and administering to the patient a retroviral vector to effect in situ transformation of lymphocytes.

Additional objects and advantages of the invention will be set forth in part in the description that follows, and in part will be obvious from the description, or may be learned by practice of the invention. The objects and advantages may be realized and obtained by means of the processes and compositions particularly pointed out in the appended claims.

BRIEF DESCRIPTION OF THE DRAWINGS

FIG. 4 shows levels of DNA synthesis occurring in vivo in patients receiving a 5-day continuous infusion of IL-2.

DETAILED DESCRIPTION OF THE PREFERRED EMBODIMENTS

Figure 1A:
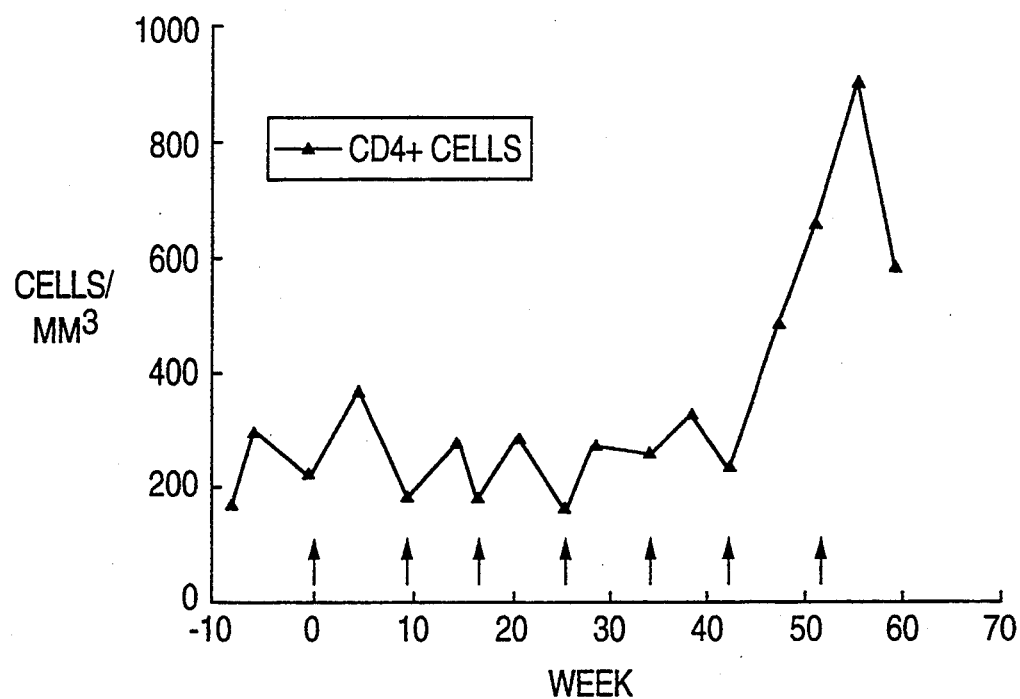
FIGS. 1A–1B show changes in CD4 cell count and blastogenic responses to tetanus toxoid and pokeweed mitogen (PWM) for patients 1 and 3 during a year of intermittent IL-2 therapy.

The present invention provides a method for increasing the level of immune function of patients, including immunosuppressed patients, by treatment with IL-2. The increase in immune function typically manifests itself as an increase in helper/inducer T-cell function. More particularly, the increased immune function can include, for example, an increase in CD4 count, a restoration of lymphocyte function and/or an increase in the expression of IL-2 receptors (IL-2r).

A method within the present invention can be effective against disease states in which IL-2 plays a role in the associated immune response. The targeted disease state can comprise, for instance, an infection of the patient by a pathogen against which a cellular immune response is the principal mechanism for specific immunity therefor in the patient, such as viral infections. See Abbas et al., CELLULAR AND MOLECULAR IMMUNOLOGY 309–310 (W. B. Saunders Co., Philadelphia 1991). Illustrative of specific disease states in treatment of which the present invention can be applied are HIV infection and other diseases characterized by a decrease of T-cell immunity, for example, mycobacterial infections like tuberculosis and fungal infections such as cryptococcal disease. This method can also be used in the treatment of secondary infections that occur in patients with suppressed immune systems, such as the opportunistic infections that occur in AIDS patients.

While prior attempts at the therapeutic use of IL-2 in treating AIDS patients have been largely unsuccessful, the method of the present invention elicits maximal T-cell activation and T-cell expansion in patients with HIV infection, and should be effective in a qualitatively similar manner in any patient. The method promotes at least partial restoration of immune function of HIV-infected patients, as demonstrated by sustained improvements in CD4 counts as well as by restoration of T-cell responsiveness to recall antigens and mitogens, with results sustained up to four months after IL-2 infusion has been stopped. CD4 levels have been restored to and sustained at levels seen in healthy patients (800–1200 cells/mm$^3$) or even higher, indicating a restoration of the immune system as a result of the IL-2 therapy.

The present invention utilizes multiple, continuous infusions of IL-2, where the infusions are administered intermittently over an extended period of time. The IL-2 is administered by continuous infusion which can be through a central line, i.e., through the neck, or peripherally, e.g., through the arm. It is an advantage of this method that the continuous IL-2 infusion can be administered peripherally. By contrast, previously disclosed low-dose continuous IL-2 treatments require central line infusions, which cause more discomfort to the patient. In addition, we anticipate that similar results will be seen with intermittent subcutaneous administration of IL-2.

The dosages of IL-2 which are characteristic of the present invention range from 1 million international units (MU)/day to 24 MU/day. These doses are much higher than doses previously used in the treatment of AIDS, but lower than those used in the treatment of cancer. In a preferred embodiment, IL-2 is administered by continuous IV infusion over 5 days, once every 8 weeks, at doses between about 6 to 18 million international units (MU)/day. Patients have been observed to show initial increases in expression of IL-2 receptors after 2 to 4 courses of this therapy. Although a dosage of 18 MU/day is preferred, some patients may not be able to tolerate this high level of IL-2, and dosages of 6–12 MU/day may be used with benefit.

The IL-2 therapy of the present invention follows an intermittent course. The IL-2 is administered continuously for period of time of from 1 day to 2 weeks. Infusion periods of less than one day will not be effective, and infusion periods of longer than 2 weeks seem to show no advantage over shorter periods. Studies have shown that peak activation of the immune system occurs at about the 5th day of IL-2 infusion, so an infusion period of about 1 week is preferred.

The time period between successive infusions can vary from 4 weeks to six months, or even one year. Infusions closer than 4 weeks apart are too close to yield the benefits of intermittent therapy, and would not be beneficial to the patient. With infusions closer than 4 weeks apart, the dosages of the present invention are not well tolerated. In light of the side effects associated with IL-2 therapy, and the need to be hospitalized for the continuous infusion treatments, longer time periods between infusions are preferred. For example, the IL-2 can be administered every 6 weeks, 8 weeks, 12 weeks, or six months, and beneficial results may be seen. It is hoped that treatments as far apart as one year or longer would show sustained beneficial results.

An optimal time period between infusions has not been determined, and would probably vary from patient to patient. One skilled in the art would be able to modify a protocol within the present invention, in accordance with conventional clinical practice, to obtain optimal results for a given patient. For example, in one study patients were continuously infused with IL-2 at the above described dosages for 5 days, no IL-2 was given for 8 weeks, and then IL-2 was again given continuously for 5 days. The cycle is continued, and patients have undergone 3-7 courses of IL-2.

The intermittent IL-2 therapy of this invention can constitute a lifelong treatment regime, with the cycles of IL-2 infusions continuing indefinitely. It is believed that once a patient's immune system has been restored by this method, as evidenced by sustained CD4 counts at or above normal levels, subsequent infusions can be administered further and further apart. For example, a patient initially receiving infusions every 8 weeks may subsequently receive infusions every 6 months, and then once a year, and still maintain elevated CD4 counts.

The intermittent administration of IL-2 may be analogous to the in vitro approach of alternating cycles of stimulation with rest needed for the establishment or expression of T-cell lines or clones (M. Kimoto & G. G. Fathman, J. Exp. Med. 152: 759-770 (1980)). IL-2 could possibly also prolong T-cell survival by altering HIV-envelope mediated programmed cell death, which may play a role in CD4 depletion in HIV infection. D. I. Cohen et al., Science 156: 542-545 (1992); H. Groux et al., J. Exp. Med. 175: 331-340 (1992) Additionally, IL-2 may be serving to alter the balance between Th1 and Th2 lymphocytes, and thus reverse the relative deficiency of Th1 cells that has recently been suggested to occur in HIV infection (H. C. Lane et al., N. Engl. J. Med. (1984); M. Clerici et al., J. Clin. Invest. 91: 759-765 (1993)).

Present studies have focused on treating HIV-infected patients with a relatively intact immune system. The degree of response of the patient to the treatment has been shown to be directly correlated to the level of immune system remaining in the patient, or inversely related to the level of the virus in the patient. The degree of remaining immune system can be measured by the T4 or CD4 count of the patient. Patients with a T4 or CD4 count above about 150 cells/mm$^3$ were found to respond well to the method of treatment of the present invention. The level of virus in the patient can be measured by vital titer. If plasma diluted at a ratio of about 1:81 is able to grow virus, the patient is not recommended for immediate treatment without concomitant anti-retroviral therapy.

Patients with viral levels too high can be first treated with ddI, AZT, or other anti-retroviral drugs to lower the viral burden. Alternatively, the anti-retroviral therapy can be administered simultaneously with the IL-2 therapy, allowing patients with weaker immune systems and higher viral burdens to benefit from the intermittent IL-2 therapy.

Another reason for administering concomitant anti-retroviral therapy to AIDS patients undergoing IL-2 therapy is the major concern that the viral burden of HIV patients receiving IL-2 therapy will be increased, since HIV replicates more readily in activated cells. To minimize the possible effects of increased viral burden, the IL-2 therapy is preferably combined with an anti-retroviral therapy. Such anti-retroviral therapy can comprise, for example, the administration of AZT, AZT and ddI, or interferon alpha. The anti-retroviral therapy can commence before the IL-2 therapy is started, and can continue throughout the course of the intermittent IL-2 therapy. When patients are receiving concomitant anti-retroviral therapy, it appears that increased viral replication occurs only in the brief interval around the infusion of IL-2. In this setting, potent agents, for example, U-90152 (Upjohn), PMEA (Gilead), and CD4-PE (Upjohn), may be used intermittently for short periods of time without the development of resistant strains of virus.

When the intermittent IL-2 therapy of the present invention is used in the treatment of disease states other than HIV infection, additional therapies which target such disease states also can be used in conjunction with the IL-2 therapy. For example, anti-bacterial agents could be used in the treatment of bacterial infections and anti-fungal agents could be used in the treatment of fungal conditions. As disclosed above with reference to anti-retroviral therapy, such treatments could be used prior to or concomitant with the intermittent IL-2 therapy of the present invention.

Progress achieved by IL-2 therapy within the present invention can be measured by many parameters. The method of the present invention boosts the helper/inducer T-cell function of the cells. The helper T-cells activate various T effector cells that generate cell-mediated responses to antigens, including an increased production of IL-2 and IL-2 receptors. See J. Kuby, IMMUNOLOGY 17-18 (W. H. Freeman and Co., New York 1992). The increase in IL-2 receptors observed in patients undergoing therapy by this method is consistent with such an elevation of helper/inducer T-cell function.

Studies have shown that in HIV-infected patients, responses of peripheral blood lymphocytes, as measured by lymphocyte blast transformation as well as by IL-2 production, tend to be lost initially to recall antigens, then to alloantigens, and finally, as immunosuppression becomes severe, to mitogens such as phytohemagglutinin and pokeweed mitogen (M. T. Lotze et al., Cancer 58: 2754-2772 (1986); H. C. Lane et al., New England J. Med. 313: 79-84 (1985); M. Clerici et al., J. Clin. Invest. 91: 759-765 ( 1993)). Although the decreased responses to alloantigens and mitogens may be at least partially explained by alteration in relative numbers of CD4 and CD8 cells placed in tissue culture, this defect in responsiveness to soluble antigens is seen even when one studies purified CD4 cells (H. C. Lane et al., New England J. Med. 313: 79-84 (1985)). In fact, one of the earliest immune defects associated with HIV infection is this loss of ability to respond to recall antigens, and is often present in patients with normal CD4 counts (H. C. Lane et al., New England J. Med. 313: 79-84 (1985)).

The ability of intermittent IL-2 therapy to restore in vitro lymphocyte function was determined. As shown in Table 2 and FIGS. 1A-1D, intermittent IL-2 therapy of the present invention was associated with an improvement in blastogenic responses in the reverse order of their probable loss.

Another phenomenon observed in HIV patients is the increased percent of human leukocyte antigen-D related (HLA-DR) positive lymphocytes compared to healthy controls. (A. Landay et al., AIDS 4: 479-497 (1990); J. V. Giorgi et al., Clin. Immunol. Immunopathol 52: 10-18 (1989)). This represents an increase in the proportion of lymphocytes in the peripheral blood that are activated and presumably terminally differentiated. This increase in HLA-DR is seen primarily in CD8 positive cells, and may be a poor prognostic sign (D. P. Sites et al., Clin. Immunol. Immunopathol 38: 161–177 (1986)). The percent of HLA-positive lymphocytes of all patients were found to be elevated prior to treatment.

As shown in FIGS. 2A–2G and Table 2, the intermittent IL-2 therapy of the present invention leads to a decline in the proportion of cells positive for HLA-DR. This decline in HLA-DR positive cells may represent an IL-2induced improvement in the aberrant homeostatic mechanisms that are regulating CD8 lymphocyte activation in HIV. These decreased levels are observed even one and two months after completion of IL-2 courses.

Levels of IL-2 receptors in CD4 positive cells and in both CD4 and CD8 cells increased during the intermittent IL-2 therapy. This up-regulation of IL-2 receptors is likely a pharmacologic effect of IL-2, and may explain why some patients had increases in CD4 but not CD8 cells, while other patients had increases in both. The increase in IL-2 receptor-expressing cells also may be responsible for the improvement in blastogenic responses, since such responses are dependent on recruitment of initially unresponsive cells, and such cells, if expressing IL-2 receptors, can respond more easily to IL-2 secreted by the initially activated cells.

Our observations differ from other reports using low doses of recombinant IL-2 or polyethylene glycol (PEG) IL-2 administered subcutaneously, in which no changes in CD4, CD8, HLA-DR, or IL-2 receptor-positive cells were seen (H. Teppler et al., J. Infect. Dis. 167: 291–298 (1993); H. Teppler et al., J. Exp. Med. 177: 483–492 (1993)). Further, while natural killer (NK) activity has been shown to increase with low doses of IL-2 (H. Teppler et al., J. Infect. Dis. 167: 291–298 (1993); M. A. Caligiuri et al., J. Clin Invest. 91: 123–132 (1993)), we observed no consistent changes in NK or LAK activity following IL-2 therapy (data not shown).

In accordance with another aspect of the present invention, a method of gene therapy is provided which takes advantage of the activated state of the immune system during the course of IL-2 treatment. In this method, the heightened level of lymphocyte activity can be used to the advantage of allowing in situ transformation of T-cells by a retroviral vector. In contrast to prior art methods of gene therapy where cells are obtained from the patient, transduced in vitro, and infused into the patient, the method of the present invention allows the direct administration of a retroviral vector to the patient, with the transduction of the cells occurring in situ.

In this method, the immune system is first activated by administering IL-2, as described above. The IL-2 induces the cells to become activated and to synthesize DNA, which makes them more receptive to transduction by retroviral vectors. A genetically-engineered retroviral vector then is administered directly to the patient. This vector is integrated with the DNA of the patient's own cells, and the administered gene is subsequently expressed. Retroviral vectors that would make a cell resistant to a virus, such as HIV, or that would make a cell able to attack a virus could be introduced into a patient's system by this method. Plasmid DNA can also be used in place of the retroviral vectors, with similar benefits and results seen.

This method is most effective when the vector is administered to the patient when cells are most susceptible to transduction by the vector. Such susceptibility occurs during periods of peak DNA synthesis, which is usually observed during the time period when the IL-2 is being administered.

FIG. 4 shows the levels of DNA synthesis occurring in vivo in seven patients receiving a 5-day continuous infusion of IL-2 at the above described dosages. Data points were taken prior to IL-2 therapy (PRE), at day 0 of the IL-2 infusions (D/0), at day 5 (D/5) of the IL-2 infusions, and at follow-up visits (F/U). Each peak corresponds to the level of DNA synthesis at day 5 of infusion. This intense in vivo T-cell activation seen at day 5 of the IL-2 infusion marks a preferred time to effect T-cell transduction by administering a retroviral vector directly to the patient.

The present invention is further illustrated by reference to the following examples, which illustrate specific elements of the invention but should not be construed as limiting the scope of the invention.

Studies of the effects of intermittent courses of IL-2 on the immune system of immunosuppressed patients were performed. The studies were approved by the National Institute of Allergy and Infectious Disease (NIAID) institutional review board, and all patients provided written informed consent after the risks of the study had been explained.

Patients with HIV infection were eligible for enrollment if they had a CD4 count above 200 cells/mm$^3$ and had no concurrent opportunistic infections. The cut-off for CD4 counts was selected based on earlier work demonstrating that this group is more likely to respond to immunomodulators than patients with severely impaired immune function.

Because of concerns that IL-2 could lead to enhanced HIV replication, anti-retroviral therapy, primarily zidovudine (AZT), was administered throughout the study. Initial evaluation included a complete history, physical exam, hematology and chemistry profiles, urinalysis, immunologic profiles, p24 antigen levels, and, in some patients, titers of plasma virus (Dewar et al., Acq. Immune Def. Syndromes, 5: 822–828 (1992); R. Davey, Jr. et al., P.N.A.S., U.S.A., in press) or quantitation of particle-associated plasma HIV RNA using a branched DNA (bDNA) assay (C. A. Pachl et al., Abstract #1247, 32nd INTERSCIENCE CONFERENCE ON ANTIMICROBIAL AGENTS AND CHEMOTHERAPY, October 1992; M. S. Urdea et al., NUCLEIC ACID RESEARCH SYMPOSIUM SERIES No. 24, pages 197–200 (Oxford University Press 1991). Laboratory evaluation was repeated at least monthly.

EXAMPLE 1. INITIAL TOXICITY TRIALS

Native and recombinant IL-2 was administered to patients by continuous infusion at doses up to 12 MU/day for a three-to-eight-week course.

These dosages of IL-2 were well-tolerated, and transient increases in CD4 counts could be seen (H. C. Lane et al., J. Biol. Response Mod. 3: 512–516 (1984)). Bone marrow biopsies obtained at the end of this continuous IL-2 therapy demonstrated a relative lymphocytosis when compared to pre-therapy samples, suggesting that effects of IL-2 were not simply the retrafficking of lymphocytes to the peripheral blood.

EXAMPLE 2. DOSAGE ESCALATION TRIAL

A dose escalation trial was performed in which 23 patients received a single 21-day or 5-day course of recombinant IL-2 (rIL-2; Chiron) by continuous infusion, at doses ranging from 1.8 million international units (MU)/day to 24 MU/day. All patients received zidovudine (100–200 mg 5id or q4h) beginning at least six weeks prior to the first IL-2 course.

The maximum tolerated dose of recombinant IL-2 when administered for 21 days in combination with zidovudine was found to be 12 MU/day, and when administered for five days in combination with zidovudine was found to be 18 MU/day. Dose-limiting toxicities were similar to those previously associated with recombinant IL-2 therapy alone (J. P. Siegel et al., J. Clin. Oncol. 9: 694–704 (1991); M. T. Lotze et al., Cancer 58: 2754–2772 (1986)) and included hepatic and renal dysfunction, thrombocytopenia, neutropenia, respiratory distress, and severe flu-like symptoms.

Transient changes were seen in CD4 counts during this phase, but no consistent long-term changes in immune parameters were seen (data not shown). No consistent changes in p24 antigen levels or ability to culture HIV from peripheral blood mononuclear cells were found.

EXAMPLE 3. INTERMITTENT IL-2 THERAPY

A multiple course study of intermittent IL-2 therapy was performed. Eight patients (six men and two women) received a five-day course of recombinant IL-2 on an inpatient basis by continuous infusion, initially at a dose of 18 MU/day, every eight weeks. Recombinant IL-2 was administered either through a central line IV or a peripheral IV. When peripheral infusions were used, the recombinant IL-2 was placed in 5% dextrose in water (D5W) containing 0.1% albumin. Zidovudine (100 mg bid) was administered concomitantly. Near the end of the study, didanosine therapy (200 mg bid) was also used in two patients.

The employed dosages of IL-2 generally were well-tolerated and were less toxic than the higher dose regimens typically used in cancer therapy. However, six patients required dosage reduction to 12 or 6 MU/day, primarily because of fever and severe flu-like symptoms. Other toxicities, including metabolic abnormalities, hepatic and renal dysfunction, hypothyroidism, thrombocytopenia, and anemia were seen but were mild and not dose-limiting.

Several parameters were used to evaluate results. Changes in lymphocyte subpopulations (CD4 percent and count, CD8 count, CD4:CD8 ratio, lymphocyte count, and CD3 count) following multiple courses of IL-2 therapy were determined. Flow cytometry was performed on Ficoll-Hypaque-separated peripheral blood mononuclear cells by previously described techniques using monoclonal antibodies to CD3 (T cell), CD4 (helper-inducer T cell), and CD8 (suppressor-cytotoxic T cell) (H. C. Lane et al., Am. J. Med. 78: 417–422 (1985)). Values used represent the mean of three pre-study values (Pre-IL-2) and the mean of the two latest values obtained four and eight weeks after the most recent course of IL-2. These results are shown in Table 1. The four-week value tended to be higher than the eight-week value for most patients.

TABLE 1

Changes in lymphocyte subsets during IL-2 therapy

| Pt. No. | Sample | CD4 Percent (% positive) | CD4 No. (Cells/mm$^3$) | CD8 No. (Cells/mm$^3$) | CD4:CD8 Ratio | Lymphocyte No. (Cells/mm$^3$) | CD3 No. (Cells/mm$^3$) |
|---|---|---|---|---|---|---|---|
| 1 | Pre-IL-2 | 20 | 458 | 1485 | 0.31 | 2303 | 2096 |
|   | Weeks 49/54 (6 doses) | 57 | 2130 | 1374 | 1.55 | 3768 | 3597 |
|   | Percent Change | 183 | 365 | −7 | 401 | 64 | 72 |
| 2 | Pre-IL-2 | 36 | 660 | 879 | 0.75 | 1846 | 1619 |
|   | Weeks 52/56 (6 doses) | 52 | 690 | 516 | 1.33 | 1338 | 1160 |
|   | Percent Change | 44 | 5 | −4 | 77 | −28 | −28 |
| 3 | Pre-IL-2 | 14 | 233 | 1037 | 0.22 | 1690 | 1407 |
|   | Weeks 56/60 (7 doses) | 18 | 765 | 3383 | 0.23 | 4256 | 4001 |
|   | Percent Change | 32 | 229 | 226 | 1 | 152 | 184 |
| 4 | Pre-IL-2 | 30 | 421 | 632 | 0.68 | 1423 | 1071 |
|   | Weeks 51/56 (7 doses) | 31 | 469 | 625 | 0.82 | 1501 | 1099 |
|   | Percent Change | 4 | 11 | −1 | 21 | 5 | 3 |
| 5 | Pre-IL-2 | 12 | 291 | 1784 | 0.16 | 2483 | 2137 |
|   | Weeks 51/55 (6 doses) | 13 | 276 | 1624 | 0.17 | 2195 | 1865 |
|   | Percent Change | 7 | −5 | −9 | 4 | −12 | −13 |
| 6 | Pre-IL-2 | 19 | 247 | 732 | 0.34 | 1320 | 1087 |
|   | Weeks 56/60 (4 doses) | 28 | 524 | 1035 | 0.71 | 1919 | 1681 |
|   | Percent Change | 47 | 112 | 41 | 110 | 45 | 55 |
| 7 | Pre-IL-2 | 42 | 871 | 776 | 1.12 | 2051 | 1656 |
|   | Weeks 26/31 (4 doses) | 58 | 1494 | 688 | 2.17 | 2575 | 2220 |
|   | Percent Change | 37 | 72 | −11 | 95 | 26 | 34 |
| 8 | Pre-IL-2 | 23 | 188 | 397 | 0.48 | 817 | 568 |
|   | Weeks 21/26 (3 doses) | 25 | 287 | 576 | 0.50 | 1140 | 798 |
|   | Percent Change | 7 | 53 | 45 | 4 | 39 | 40 |

Figure 1B:
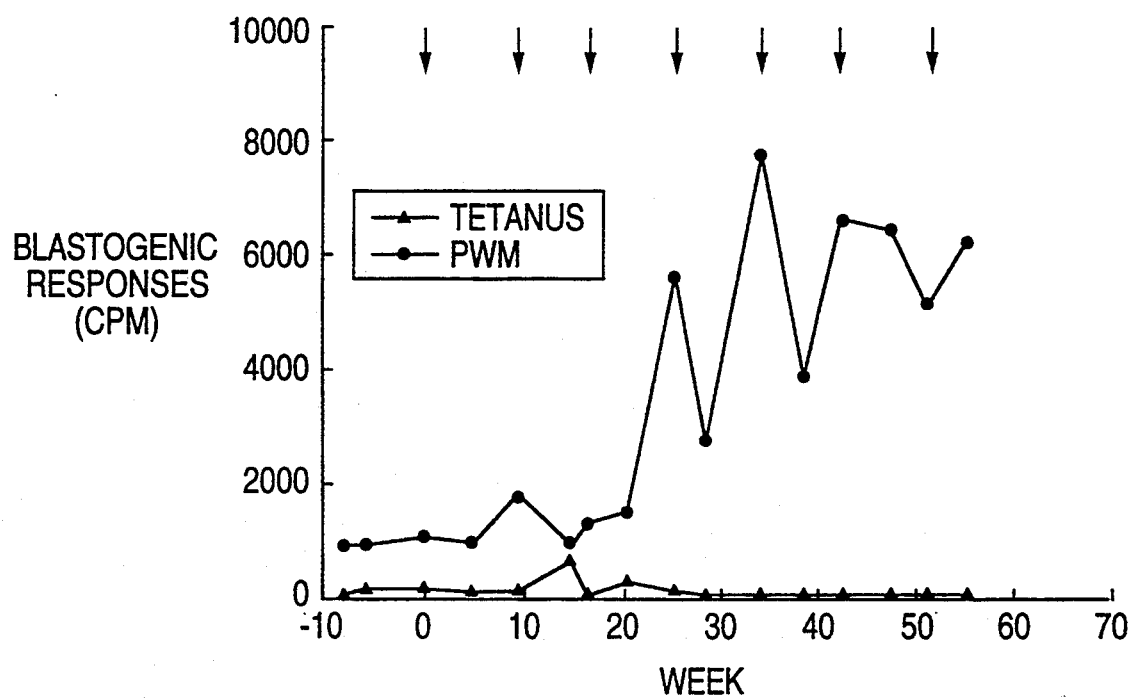

Six of the eight patients showed a consistent and sustained increase of greater than 25% in CD4 number and/or percent (Table 1 and FIGS. 1A–1D). The most dramatic increase was from 20% and 458 cells/mm$^3$ (mean of 3 values) pre-therapy to 57% and 2130 cells/mm$^3$ (mean of 2 values) one year later, after completion of six courses of recombinant IL-2 (FIGS. 1A and 1B).

Changes in CD8 number were more variable, and not necessarily concordant with changes in CD4 number. Four patients showed an increase (>25%) in the CD4:CD8 ratio due predominantly to an increase in CD4 cells (Table 1).

The immediate effects of recombinant IL-2 therapy on peripheral blood CD4 count, measured within 24 hours of discontinuation of therapy, were even more dramatic than the long-term effects measured weeks later. Peak CD4 counts of greater than 2000 cells/mm$^3$ were commonly seen, though these increases were transient (data not shown) and probably reflective of redistribution phenomena.

Changes in immunologic parameters were also determined. To evaluate the ability of intermittent IL-2 therapy to restore in vitro lymphocyte function, blastogenic responses to antigens and mitogens were measured. Proliferation assays were performed as previously described (H. C. Lane et al., Am. J. Med. 78: 417–422 (1985)), using a 1:800 dilution of PWM, or 3 $\mu$/ml of tetanus toxoid in six day, tetanus toxoid and pokeweed mitogen induced lymphocyte blast transformation assays. Values used represent the mean of three pre-study values (Pre-IL-2) and the mean of the two latest values obtained four and eight weeks after the most recent course of IL-2. The results are shown in Table 2 as net CPM of incorporated [3H]-thymidine. Percent of cells positive for IL-2 receptor (IL-2r) and human leukocyte antigen-D related (HLA-DR) expression were determined by single-color fluorescent activated cell sorter (FACS) analysis using monoclonal antibodies to CD25 (p55 IL-2 receptor) and HLA-DR. FACS analysis was gated for lymphocytes. These results are also presented in Table 2.

genic responses. This same patient also showed only a minimal decrease in the proportion of cells positive for HLA-DR.

Based on two-color FACS analysis in three patients, CD8 positive cells were the predominant population positive for HLA-DR prior to study, and were the primary population accounting for the decline in this marker (FIGS. 2B–2G). IL-2 receptors (IL-2r) increased during IL-2 therapy almost exclusively in CD4 positive cells in patients 1 and 2 (FIGS. 2B–2G), while patient 3 showed an increase in IL-2r in both CD4 and CD8 cells. This up-regulation of IL-2r is likely a pharmacologic effect of IL-2, and may explain why patients 1 and 2 had increases in CD4 but not CD8 cells, while patient 3 had increases in both.

FIGS. 1A–3J show additional results for the individual patients.

FIGS. 1A–1D show changes in CD4 cell count and blastogenic responses to tetanus toxoid and PWM for patients 1 and 3 during a year of intermittent IL-2 therapy. Arrows indicate the start of each five-day course of continuous infusion IL-2 at an initial dose of 18 MU over 24 hours. Values shown represent results obtained

TABLE 2

Changes in markers of lymphocyte function and activation during IL-2 therapy

| Pt. No. | Sample | Tetanus (CPM) | PWM (CPM) | IL-2r (% positive) | HLA-DR (% positive) |
|---|---|---|---|---|---|
| 1 | Pre-IL-2 | 2003 | 1757 | 8 | 43 |
|   | Weeks 49/54 (6 doses) | 8479 | 5981 | 53 | 23 |
|   | Percent Change | 323 | 240 | 585 | −47 |
| 2 | Pre-IL-2 | 118 | 1762 | 5 | 50 |
|   | Weeks 52/56 (6 doses) | 4250 | 12321 | 33 | 31 |
|   | Percent Change | 3512 | 599 | 509 | −38 |
| 3 | Pre-IL-2 | 212 | 1043 | 5 | 35 |
|   | Weeks 56/60 (7 doses) | 100 | 5760 | 30 | 16 |
|   | Percent Change | −53 | 452 | 500 | −56 |
| 4 | Pre-IL-2 | 117 | 1195 | 8 | 32 |
|   | Weeks 51/56 (7 doses) | 100 | 14216 | 23 | 22 |
|   | Percent Change | −15 | 1090 | 176 | −31 |
| 5 | Pre-IL-2 | 100 | 1386 | 5 | 47 |
|   | Weeks 51/55 (6 doses) | 483 | 1980 | 8 | 42 |
|   | Percent Change | 383 | 43 | 60 | −11 |
| 6 | Pre-IL-2 | 1735 | 4720 | 10 | 32 |
|   | Weeks 56/60 (4 doses) | 895 | 5944 | 25 | 30 |
|   | Percent Change | −48 | 26 | 150 | −9 |
| 7 | Pre-IL-2 | 32054 | 12568 | 8 | 21 |
|   | Weeks 26/31 (4 doses) | 39708 | 14041 | 36 | 13 |
|   | Percent Change | 24 | 12 | 326 | −38 |
| 8 | Pre-IL-2 | 121 | 19103 | 8 | 20 |
|   | Weeks 21/36 (3 doses) | 100 | 7878 | 26 | 19 |
|   | Percent Change | −17 | −59 | 206 | −3 |

As shown in Table 2 and FIGS. 1A–1D, IL-2 therapy was associated with an improvement in blastogenic responses in the reverse order of their probable loss. Thus, four of five (80%) patients with absent or poor responses to PWM developed vigorous and consistent responses during the study, and two of the seven nonresponders (29%) to the recall antigen tetanus toxoid became consistent responders.

The percent of lymphocytes positive for HLA-DR was found to be elevated ($\geq$20%) in all eight patients prior to study (Table 2). Interestingly, during IL-2 therapy, there was a decline ($\geq$25% of initial values) in the proportion of cells positive for HLA-DR, measured one and two months after completion of IL-2, in ⅝ patients (Table 2 and FIGS. 2A–2G). At the same time, the proportion of cells positive for the IL-2 receptor (IL-2r) (p55) increased progressively (Table 2 and FIGS. 2A–2G) in all patients. In one patient, this increase was minimal (patient 5, Table 2) and in this patient there was little evidence of improvement in CD4 counts or blastofour and eight weeks after each course of IL-2 with the week eight sample drawn immediately before beginning the next round of IL-2.

FIGS. 1A and 1B show the results for patient 1, who demonstrated a marked increase in CD4 cells as well as sustained improvement in lymphocyte blast transformation to both stimuli. The last data point is 15 weeks after the sixth course of IL-2 (week 59) at which point the patient's CD4 count remained above 1500 cells/mm$^3$.

Figure 1C:
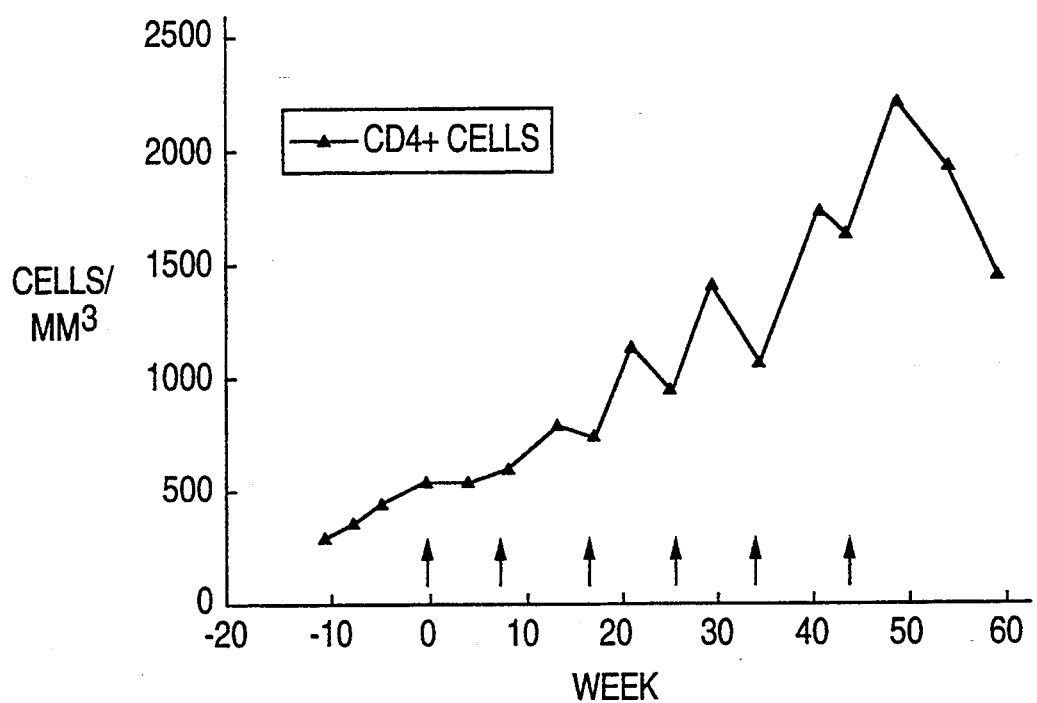
Figure 1D:
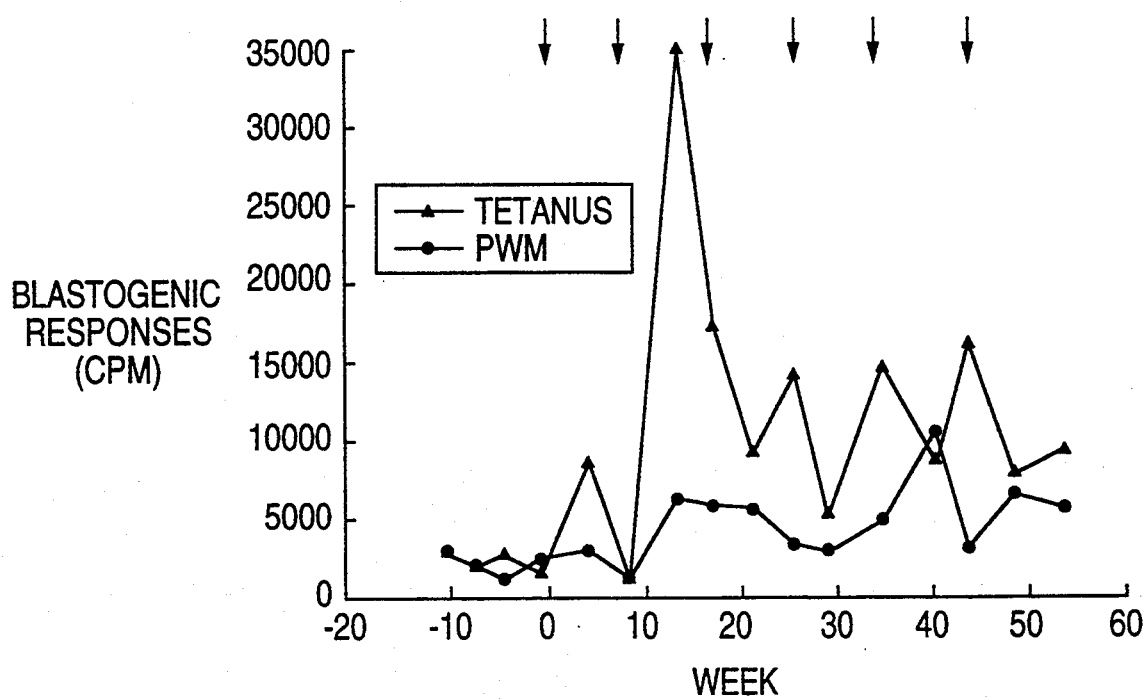

FIGS. 1C–1D show the results for patient 3, who demonstrated improvement in lymphoid blast transformation to PWM, but not tetanus toxoid. His CD4 count remained stable until after the sixth course of IL-2, at which time it increased. Didanosine was added to this patient's anti-retroviral regimen at week 38.

Figure 2A:
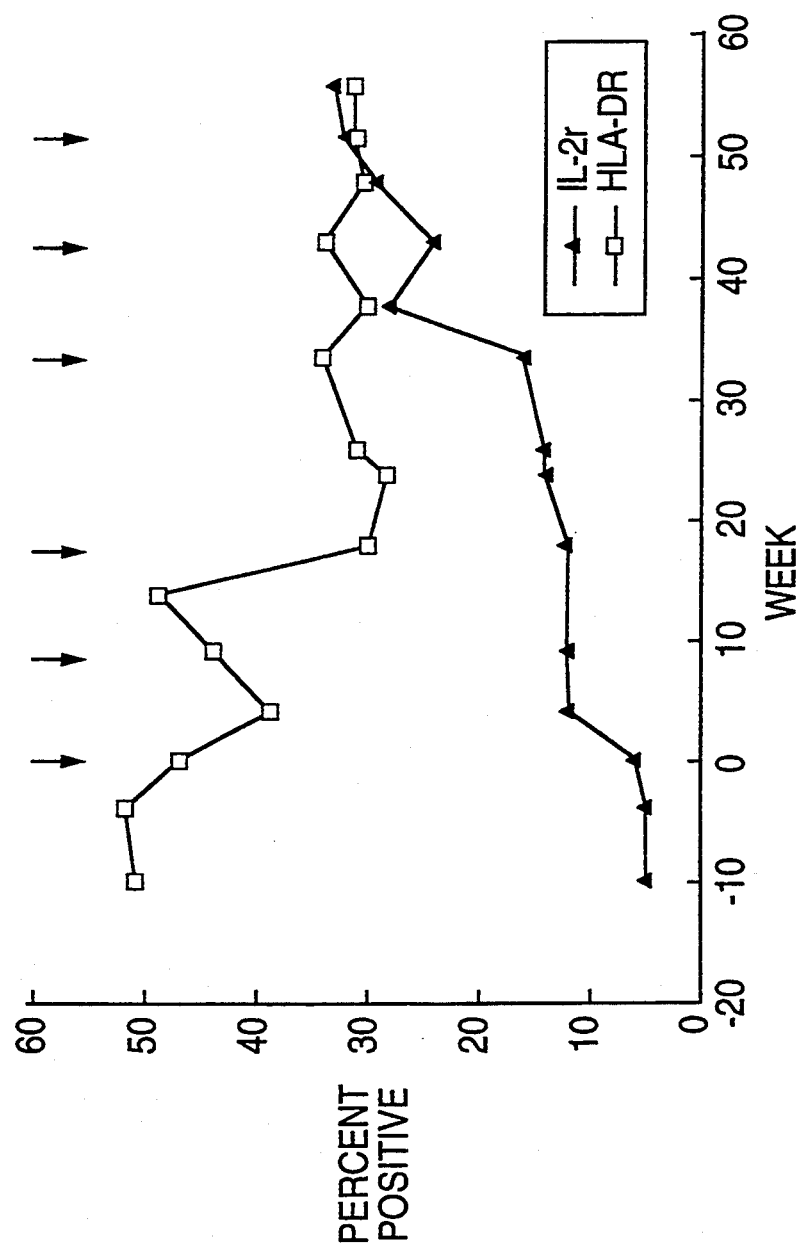
FIG. 2A shows changes in lymphocyte cell surface expression of IL-2 receptors (CD25) and human leukocyte antigen-D related (HLA-DR) expression for patient 2 during a year of IL-2 therapy.
Figure 2G:
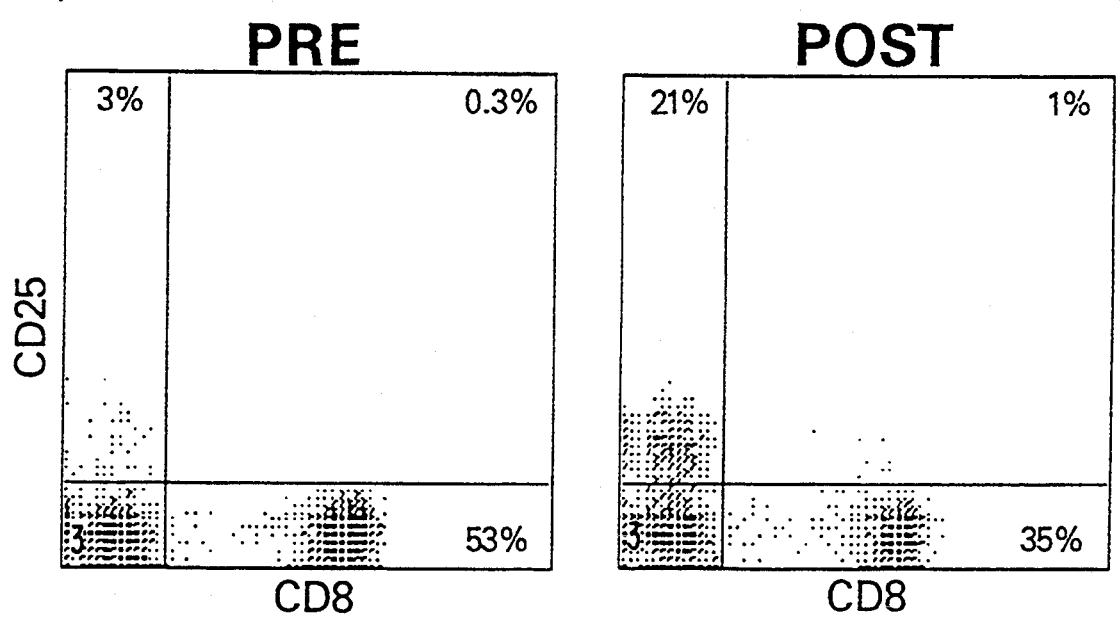
FIG. 2B–2G shows a two-color fluorescent activated cell sorter (FACS) analysis of IL-2 receptor and HLA-DR expression determined on frozen cells of patient 2 obtained prior to IL-2 therapy, and at week 48 (five weeks after the fifth course of IL-2).
Figure 2B:
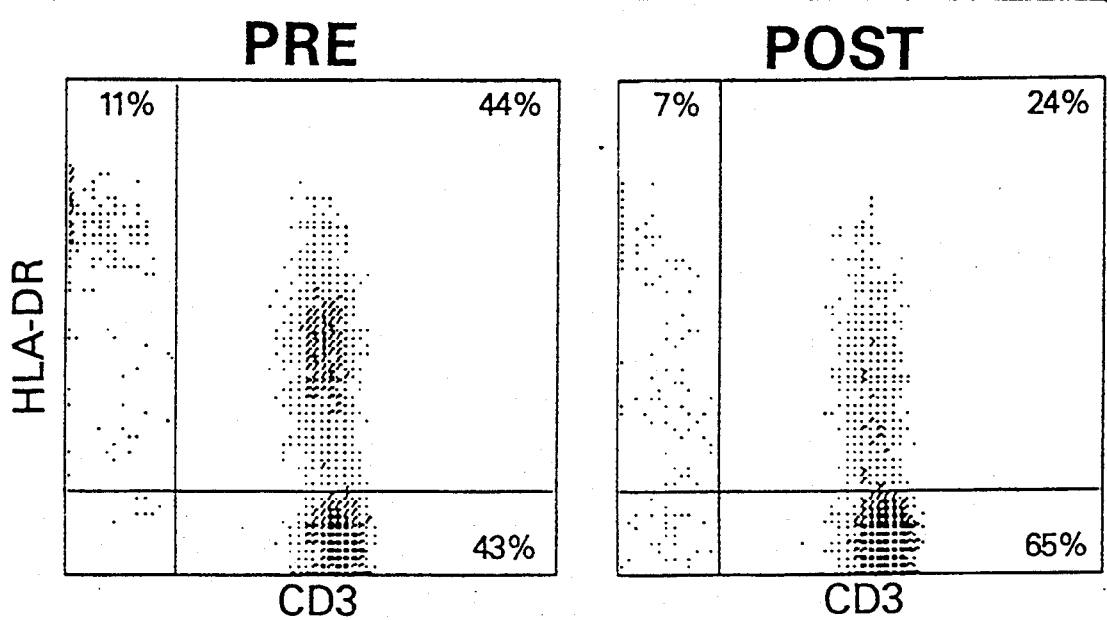
Figure 2C:
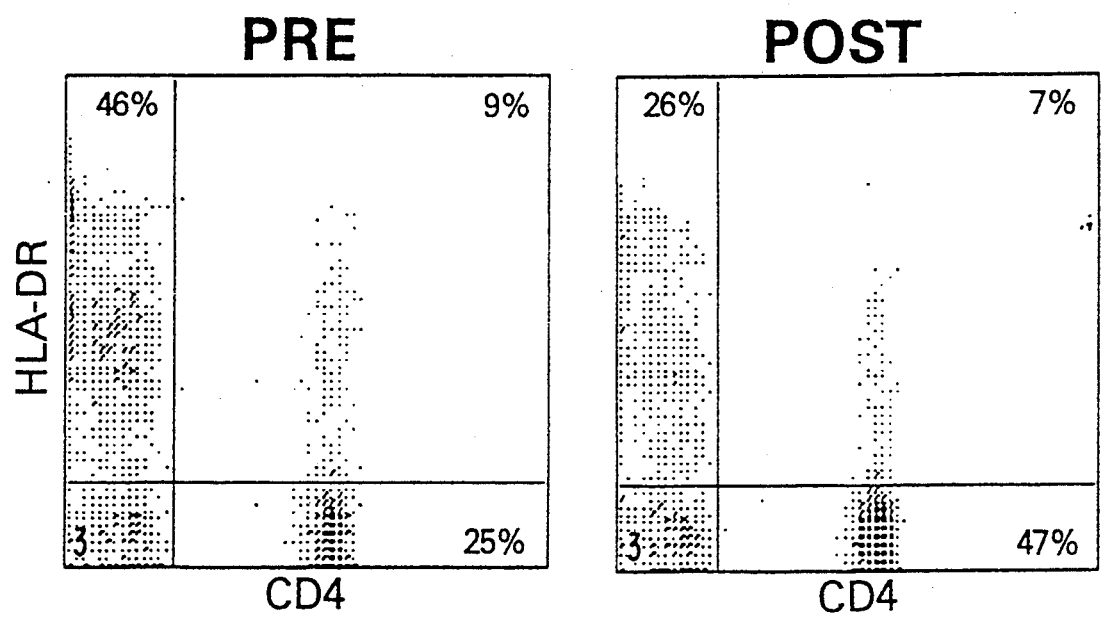
Figure 2D:
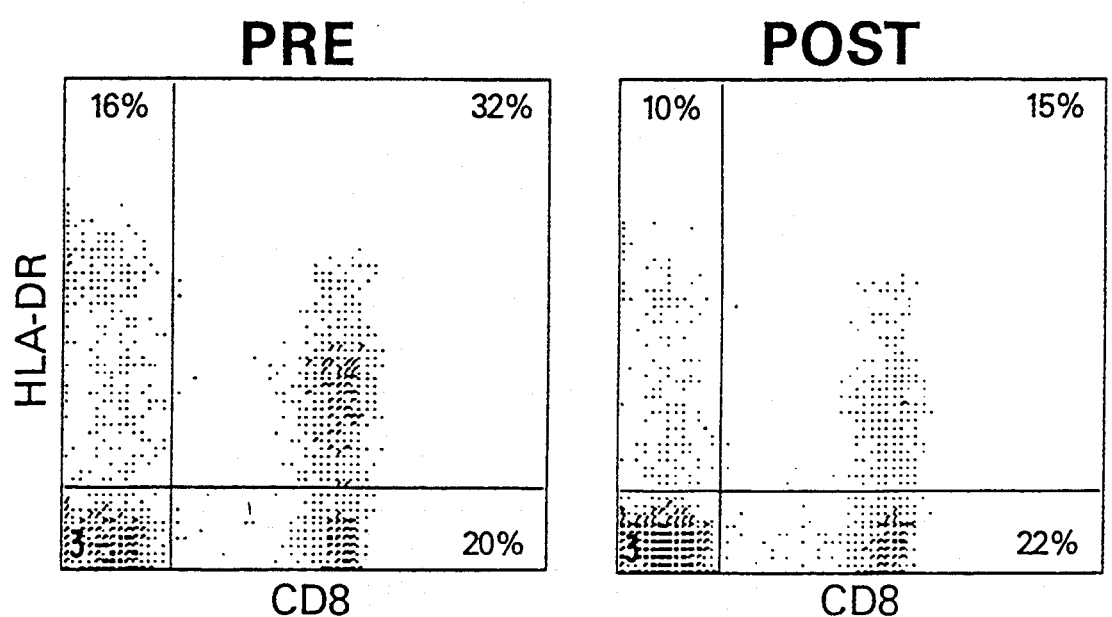
Figure 2E:
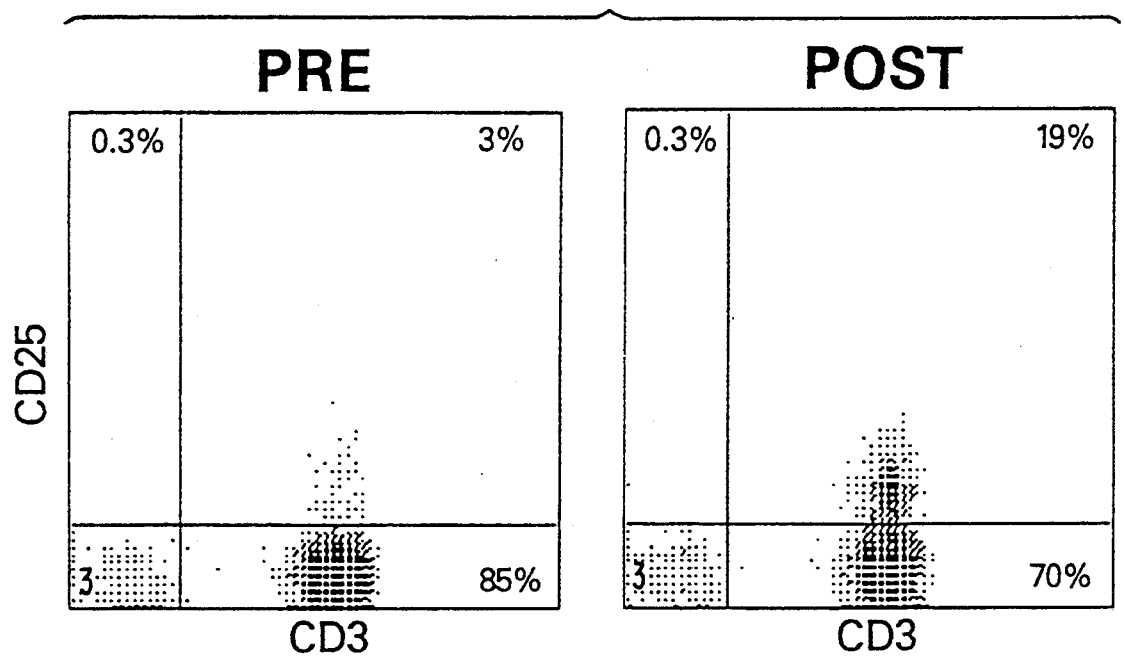
Figure 2F:
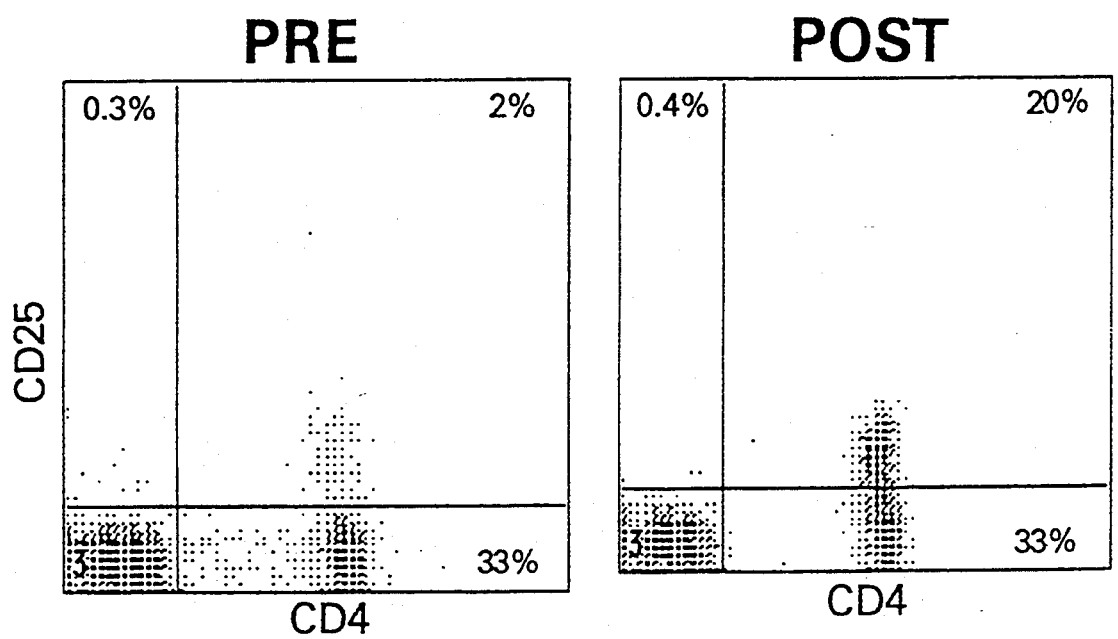
Figure 3A:
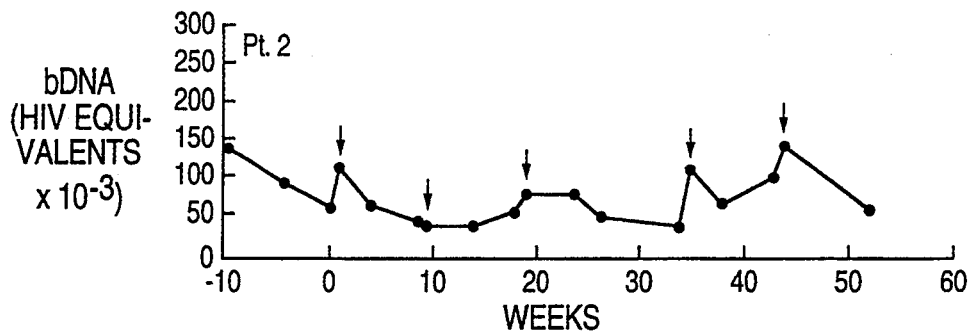
FIG. 3A–3J show changes in viral markers during IL-2 therapy for patients 2, 3, 4, 6 and 8.
Figure 3B:
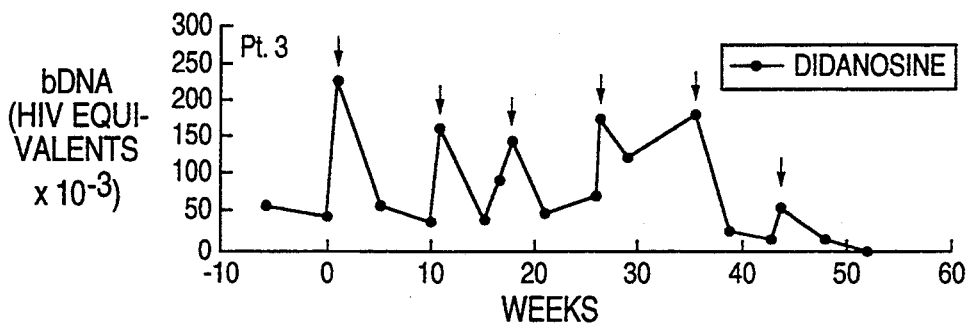
Figure 3C:
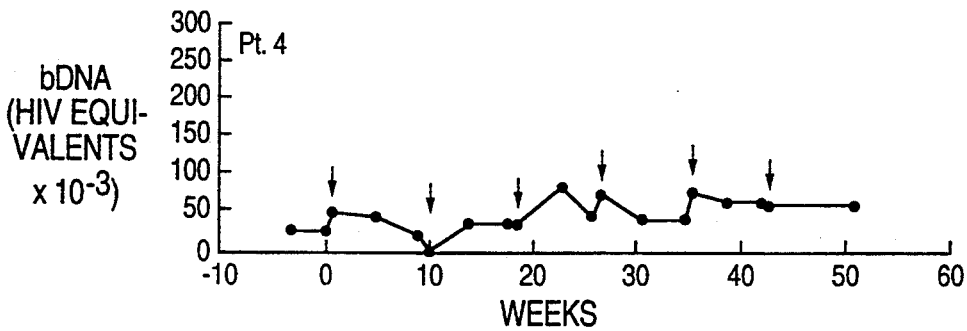
Figure 3D:
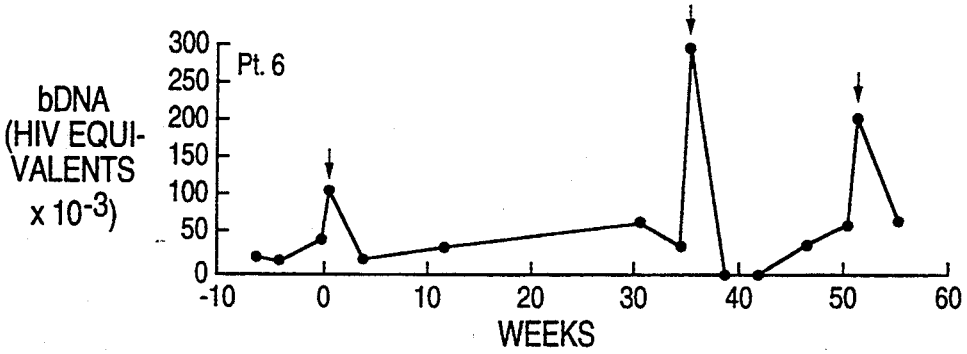
Figure 3E:
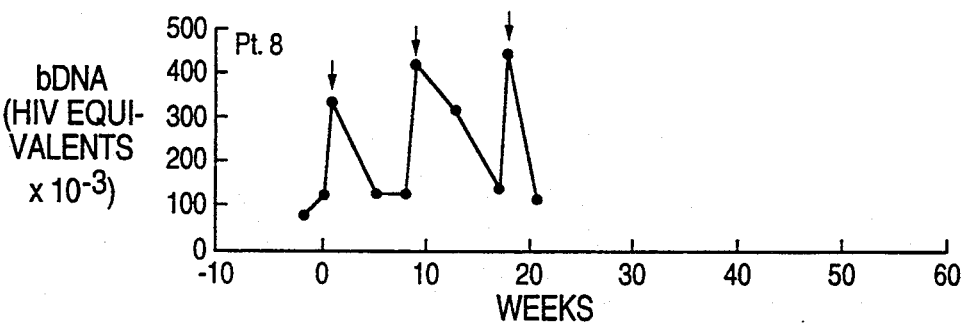
Figure 3F:
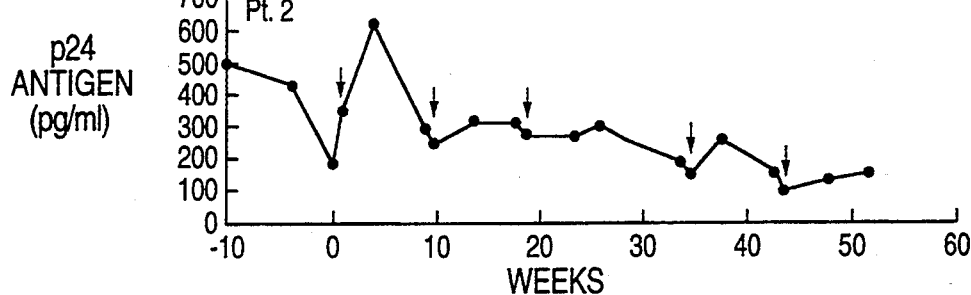
Figure 3G:
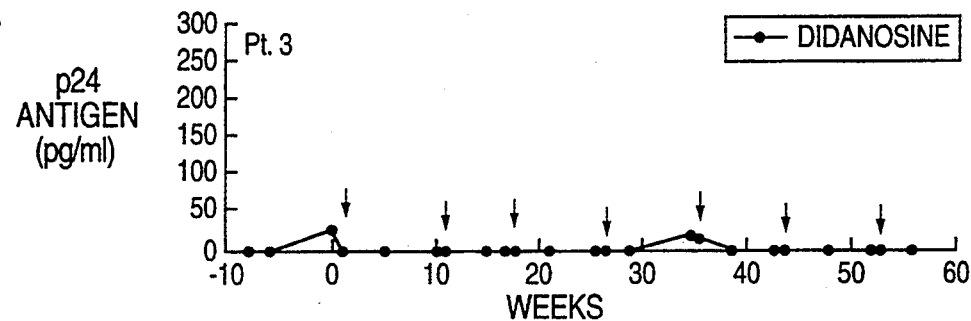
Figure 3H:
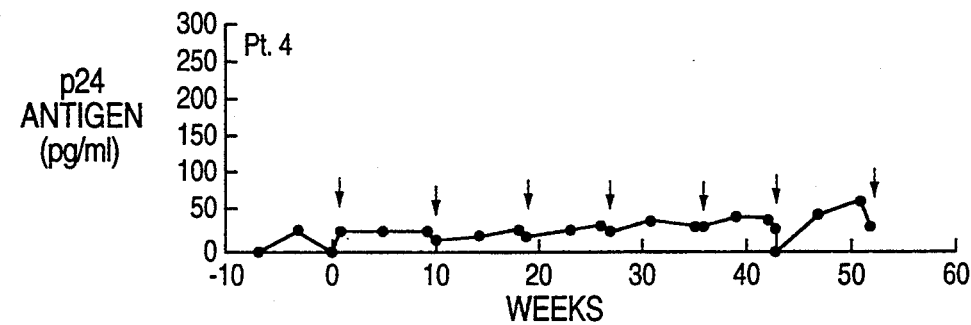
Figure 3I:
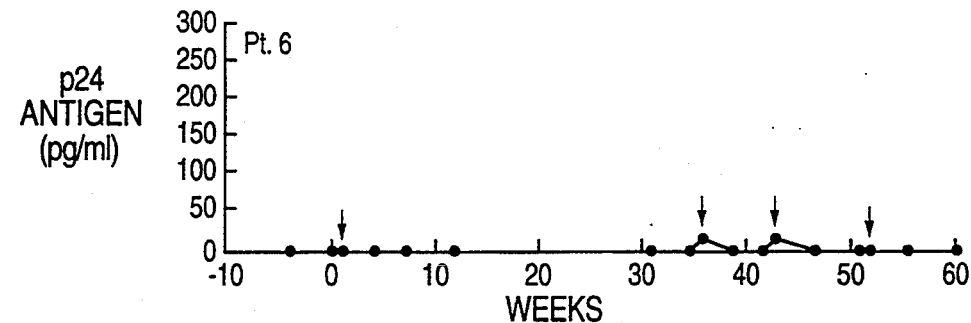
Figure 3J:
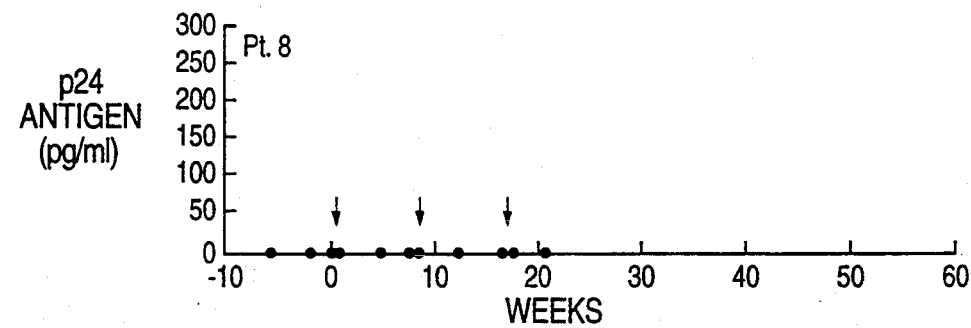

FIG. 2A shows changes in lymphocyte cell surface expression of IL-2 receptors (CD25) and HLA-DR for patient 2 during a year of IL-2 therapy. Results shown were obtained by single-color FACS analysis using monoclonal antibodies as described in Table 2, on samples obtained four and eight weeks after a course of IL-2. Arrows indicate the beginning of each course of IL-2. A sustained drop in the percentage of HLA-DR positive cells began after the second course of IL-2. The percentage of IL-2 receptor-positive cells increased substantially after four courses of IL-2.

FIGS. 2B-2G show two-color FACS analysis of IL-2 receptor (IL-2r) and HLA-DR expression determined on frozen cells of patient 2 obtained prior to IL-2 therapy, and at week 48 (five weeks after the fifth course of IL-2). As shown, the increase in IL-2r in this patient was due to increased expression exclusively on CD4 cells, while the decline in HLA-DR expression was due primarily to a decrease in expression on CD8 cells. Normal values for CD3+/IL-2r+ cells are 4.4±1.5%, and for CD3+/HLA-DR+ cells are 8.7±2.9%.

FIGS. 3A-3J show changes in viral markers during IL-2 therapy for patients 2, 3, 4, 6 and 8. Results are shown for samples obtained four and eight weeks after each course of IL-2, as well as those obtained five or six days after (arrows) beginning each five-day course of IL-2. Levels of p24 antigen levels were determined by an immune complex dissociated assay (Coulter Corporation, Hialeah, Fla.) and particle-associated HIV RNA levels were determined on frozen samples using the bDNA signal amplification assay (Chiron Corporation, Emeryville, Calif.). C. A. Pachl et al., Abstract 1247, 32nd INTERSCIENCE CONFERENCE ON ANTIMICROBIALAGENTSAND CHEMOTHERAPY, October 1992; M. S. Urdea et al., NUCLEIC ACID RESEARCH SYMPOSIUM, Series 24, Oxford University Press, pages 1927-200 (1991).

Briefly, virus was concentrated from plasma using a bench top microcentrifuge (Heraeus Contifuge Model 17RS, rotor 3753; 23,500×g, 1 hour). The resultant virus pellet was lysed with 220 µl of a proteinase K/lithium lauryl sulfate buffer containing target probes complementary to polgene sequences and then transferred to microwells of a 96-well plate. The RNA target was captured onto the microwell surface via specific capture probes during an overnight incubation at 53° C. The wells were washed and successively hybridized with the branched DNA amplifier (30 minutes), then alkaline phosphatase labeled probe (15 minutes). Finally, a chemiluminescent substrate, dioxetane, was added to each well and the enzyme-triggered light output was measured with a luminometer. The quantity of HIV RNA (reported as RNA equivalents/ml plasma) was calculated based on comparison to a standard curve. Signal was directly proportional to the amount of viral RNA present in the specimen. Not all samples were available at all time-points.

FIGS. 3A-3E show that no significant changes were seen in p24 antigenemia during IL-2 therapy. FIGS. 3F-3J show that particle-associated plasma HIV RNA tended to increase transiently immediately after IL-2 therapy (arrows), then returned to baseline. All patients were receiving zidovudine throughout the study. In patient 3, the addition of didanosine at week 38 was associated with a substantial and sustained decrease in plasma particle-associated RNA levels.

No consistent changes in overall viral load in the peripheral blood, as evaluated by serial measurement of p24 antigen levels (FIGS. 3A-3E) or plasma viremia (data not shown), were detected during multiple-course IL-2 therapy. One patient showed a gradual decline, and two a gradual increase, in p24 antigen levels during a year of therapy. The other five patients remained consistently negative for p24 antigenemia.

Because p24 antigen levels do not appear sensitive to acute changes in plasma viral burden, we assayed frozen plasma from six patients using a recently developed branched DNA assay that quantitatively measures HIV RNA (FIGS. 3F-3J). See C. A. Pachl et al., supra; M. S. Urdea et al., supra. In most patients, a consistent increase in particle-associated HIV RNA was noted immediately at the end of a course of IL-2; this increase was not associated with an increase in p24 antigen levels, and was almost always transient, with a return to baseline at the one- and two-month follow-up visits. The clinical significance of this transient burst in viral RNA is uncertain at present, but it likely represents release of HIV following activation of lymphocytes. Alternatively, it could represent a redistribution of virus from lymph nodes or other sites to the blood (G. Pantaleo et al., Nature 36: 365-371 (1993)).

In summary, six patients showed a sustained increase in CD4 number and/or percent following IL-2 therapy, with one patient increasing from 458 cells/mm$^3$ to 2130 cells/mm$^3$ during the first year of therapy. In addition to increased numbers of CD4 cells, measurements of CD4 function also showed improvement. Four of five initially unresponsive patients developed blastogenic responses to pokeweed mitogen, and two of seven initially unresponsive patients developed responses to tetanus toxoid. Thus, IL-2 therapy according to the present invention resulted in a decline in the percentage of lymphocytes expressing HLA-DR, and in an increase in the percentage of CD4 lymphocytes positive for the p55 IL-2 receptor. While no changes in HIV load were detected by p24 antigen and plasma viremia assays, a transient but consistent increase in plasma HIV RNA was detected by a new, sensitive branched DNA assay at the end of each infusion.

The patients had three to seven courses of IL-2, and follow-up ranged from 26 to 60 weeks. No patient developed an AIDS-defining opportunistic infection while on study. Accordingly, the use of IL-2 pursuant to the present invention reversed serious immunological abnormalities which are characteristic of HIV infection, especially CD4 cell depletion.

EXAMPLE 4. COMBINED IL-2/GENE THERAPY

Interleukin-2 would be given as a continuous infusion at a dose of 6-18 MU/day for a period of six days. At day 5 of the IL-2 infusion the patient would be administered intravenously with a replication-defective, amphotropic retrovirus or with plasmid DNA containing a gene that will render cells resistant to HIV infection. Due to the state of activation of the cells (FIG. 4), the genetic information of the retrovirus or the plasmid is incorporated into the genetic information of the cell, rendering that cell resistant to HIV infection.

This method also could be used to broaden the antigen-specific repertoire of the immune system by using recombinant retroviruses or plasmids that contain genetic information for specific antigen receptors.

What is claimed is:

1. A method for activating the immune system of a patient, comprising the step of administering an amount of IL-2 to said patient that is sufficient to increase the level of helper/inducer T-cell function in said patient, wherein:

(A) said IL-2 is administered in a series of infusions effected intermittently, (B) each of said infusions is continuous over a period of time of from 1 day to 2 weeks, and (C) successive infusions are separated by a period of time of at least 4 weeks.

2. A method as claimed in claim 1, wherein said amount is sufficient to increase CD4 count in said patient.

3. A method as claimed in claim 1, wherein each of said infusions comprises a dosage of IL-2 of from 1.8 to 24 MU/day.

4. A method as claimed in claim 3, wherein said period of time of each of said infusions is on the order of 5 days.

5. A method as claimed in claim 1, further comprising administering zidovudine to said patient prior to or concomitantly with said administering of IL-2.

* * * * *

UNITED STATES PATENT AND TRADEMARK OFFICE
CERTIFICATE OF CORRECTION

PATENT NO. : 5,419,900
DATED : May 30, 1995
INVENTOR(S) : H. Clifford Lane and Joseph A. Kovacs It is certified that error appears in the above-identified patent and that said Letters Patent is hereby corrected as shown below:

Title page, item [75], the correct inventors should read

--H. Clifford Lane, Bethesda; Joseph A. Kovacs, Potomac, both of Md.; Anthony S. Fauci, Washington, D.C.--.

Signed and Sealed this

Fifth Day of May, 1998

*Attest:*

BRUCE LEHMAN

*Attesting Officer*  *Commissioner of Patents and Trademarks*